US006740524B1

United States Patent
Akuta et al.

(10) Patent No.: US 6,740,524 B1
(45) Date of Patent: May 25, 2004

(54) NUCLEIC ACID TRANSFER PHAGE

(75) Inventors: Teruo Akuta, Kumamoto (JP); Haruhiko Yokoi, Tokyo (JP); Hajime Okuyama, Hyogo (JP); Katsuo Takeda, deceased, late of Tokyo (JP), by Eiko Takeda, legal representative; Mamoru Hasegawa, Ibaraki (JP); Mahito Nakanishi, Osaka (JP)

(73) Assignee: DNAVEC Research, Inc. (JP)

( * ) Notice: Subject to any disclaimer, the term of this patent is extended or adjusted under 35 U.S.C. 154(b) by 0 days.

(21) Appl. No.: 09/720,003

(22) PCT Filed: Jun. 18, 1999

(86) PCT No.: PCT/JP99/03272

§ 371 (c)(1),
(2), (4) Date: Sep. 4, 2001

(87) PCT Pub. No.: WO99/66061

PCT Pub. Date: Dec. 23, 1999

(30) Foreign Application Priority Data

Jun. 18, 1998 (JP) ............................................ 10/189845

(51) Int. Cl.$^7$ ........................ C12N 15/86; C12N 15/62; C12N 1/21; C12N 5/10; C07K 19/00
(52) U.S. Cl. ..................... 435/456; 530/350; 435/320.1; 435/252.3; 435/252.33; 435/235.1; 435/69.7; 435/975; 536/23.4
(58) Field of Search ..................... 530/350; 435/235.1, 435/320.1, 252.33, 456, 69.7, 975; 536/23.4; 424/93.2

(56) References Cited

FOREIGN PATENT DOCUMENTS

| EP | 0962525 | * 12/1999 | ............ C12N/7/01 |
| WO | 98/06828 | * 2/1998 | ............ C12N/7/01 |

OTHER PUBLICATIONS

Georgopoulos et al. Lambdoid Phage Head Assembly. In: Lambda II, ed. Hendrix et al, Cold Spring Harbor Laboratory, Cold Spring Harbor, NY. 1983. pp. 279–304.*

Hoffman et al. Biochemical and Biophysical Research Communications 235: 806–811 (1997).*

Braddock et al., "A Nuclear Translational Block Imposed by the HIV–1 U3 Region Is Relieved by the Tat–TAR Interaction," Cell 62:1123–1133 (1990).

Derossi et al., "Cell Internalization of the Third Helix of the Antennapedia Homeodomain Is Receptor–independent," The Journal of Biological Chemistry 271:18188–18193 (1996).

(List continued on next page.)

Primary Examiner—Mary E. Mosher
(74) Attorney, Agent, or Firm—Clark & Elbing LLP

(57) ABSTRACT

The present invention provides a novel phage expressing in its head a bi-functional protein that has nuclear translocation and cell adhesion activities. The phage is used to package a foreign substance such as a gene. As a bi-functional protein, TAT protein of HIV can be used. The phage is useful in gene therapy.

18 Claims, 8 Drawing Sheets

HIV-TAT(43-60)          gpD

MLGISYGRKKRRQRRRPPQT

OTHER PUBLICATIONS

Efthymiadis et al., "The HIV-1 Tat Nuclear Localization Sequence Confers Novel Nuclear Import Properties," *The Journal of Biological Chemistry* 273:1623–1628 (1998).

Elliott et al., "Intercellular Trafficking and Protein Delivery by a Herpesvirus Structural Protein," *Cell* 88:223–233 (1997).

Joliot et al., "Antennapedia Homebox Peptide Regulates Neural Morphogenesis," *Proc. Natl. Acad. Sci, USA* 88:1864–1868 (1991).

Lewin et al., "Tat Peptide–Derivatized Magnetic Nanoparticles Allow in vivo Tracking and Recovery of Progenitor Cells," *Nature Biotechnology* 18:410–414 (2000).

Mayer et al., "HIV-1 Tat Modulates Invasion by a Bacterial Enteric Pathogen into a Human Intestinal Cell Line," *AIDS* 9:1237–1242 (1995).

Schwarze et al., "In Vivo Protein Transduction: Delivery of a Biologically Active Protein into the Mouse," *Science* 285:1569–1572 (1999).

Schwarze et al., "Protein Transduction: Unrestricted Delivery into all Cells?," *Trends in Cell Biology* 10:290–295 (2000).

Vivès et al., "A Truncated HIV–1 Tat Protein Basic Domain Rapidly Translocates through the Plasma Membrane and Accumulates in the Cell Nucleus," *The Journal of Biological Chemistry* 272:16010–16017 (1997).

* cited by examiner

HIV-TAT(43-60)        gpD

MLGISYGRKKRRQRRRPPQT

STEP 1. Introduction of Dam15 into left arm of λgt11

STEP 2. λD1180 construction (80% genome size)

STEP 3. Insertion of CMV-GFP gene into λD1180

STEP 4. *E.coli* lysogenization and phage preparation

...

NUCLEIC ACID TRANSFER PHAGE

This application claims priority from international patent application serial number PCT/JP99/03272, filed on Jun. 18, 1999, which, in turn, claims priority from Japanese patent application serial number JP 10/189845, filed Jun. 18, 1998, the disclosures of which are hereby incorporated by reference.

TECHNICAL FIELD

The present invention belongs to the gene engineering, and relates to a technique for transporting a foreign substance such as nucleic acid by using virus particles, in particular.

BACKGROUND ART

The technology by which a foreign gene is delivered into animal cells is important for analysis of various biological phenomena, and for practical applications including gene therapy and creation of valuable animals. There are two major categories among the techniques used for DNA transfer: one is a biological approach relying on recombinant animal viruses carrying a foreign gene, and the other is a non-biological approach relying on physical force for delivering DNA into cells.

The former based on a principle by which recombinant viruses deliver their genome into the cells and integrate the viral genome into the host genome. This strategy is currently employed as a principal technique for gene therapy of Lesch-Nyhan syndrome and of adenosine deaminase (ADA) deficiency.

The strategies dependent on recombinant viruses, however, have been criticized for many disadvantages including pathogenicity of its own because it utilizes the biological features of intact viruses. In case of recombinant retrovirus vectors, the sequences involved in pathogenicity or replication are deleted from their genome for vector production. Nevertheless, gene-engineered vectors have still potentials of recovering infectivity through homologous recombination with endogenous retrovirus sequence in host cell genome. In addition, retrovirus vectors can only be applied to dividing cells due to the characteristics of the life cycle of the virus. Adenovirus vector, another virus vector, is proved to be effective in delivering genes into non-dividing cells like neurons. However, this vector has other problems in cytotoxicity and ntigenicity. The need of cultured mammalian cells for viral vector production is thought to be another disadvantage of viral vectors in terms of manufacturing.

Accordingly, non-viral strategies for DNA delivery have been used in parallel with those relying on recombinant viruses. Various methods have been established, in which purified DNA was delivered into the cells with the help of cationic compounds such as calcium phosphate, DEAE-dextran, cationic polymer and cationic liposome. However, due to a number of reasons, the transfection efficiency of these procedures is generally very low, comparing to the strategies using recombinant viruses. For example, the efficiency of nuclear delivery of DNA is quite insufficient in non-viral strategies. Thus, these non-viral strategies also have many disadvantages, which have to be overcome for the medical application such as gene therapy.

Gene delivery into mammalian cells consists of the following three major steps. Firstly, genetic materials should adsorb to and traverse across the cell membrane. Secondly, genetic materials should be transported from the cytoplasm into the nucleus. Thirdly, genetic materials should be properly transcribed to messenger RNA in the nucleus. Furthermore, if the genetic material is a piece of nucleic acid used for controlling the expression of endogenous genes, it should be localized to the site of transcription properly. All of these steps are processed relatively efficiently in the retrovirus-mediated gene transfer systems but inefficiently in non-viral gene delivery systems.

In order to improve the efficiency of gene transfer by non-viral delivery systems, scientists have tried to obtain the clues to facilitate each of these steps. For facilitating the nuclear delivery of a gene, application of nuclear localization signal (NLS) has been investigated. NLS is a stretch of amino acid residues that functions as a transport signal to the nucleus (Garcia-Bustos G. et al. Biochem. Biophys. Acta 1071:83–101 (1991)). It has been reported that NLS could promote the nuclear transport of various cytoplasmic proteins when attached to these proteins covalently or with recombinant DNA technology (Lanford R. E. et al. Cell 46:575–582 (1986); Yoneda Y. et al. Exp. Cell Res. 170:439–452 (1987); Chelsky D. et al. Mol. Cell. Biol. 9:2487–2492 (1989)). In most of the approaches to facilitate the nuclear delivery of DNA, NLS was attached to the DNA packed into a complex as small as the inner diameter of the nuclear pore. Poly-L-lysine (Perales J. C. et al. Eur. J. Biochem. 266:255–266 (1994)) and cationic lipids (Zabner J. et al. J. Biol. Chem. 270:18997–19007 (1995)) has been employed to pack the DNA, as well as proteins such as HMG-1 and histons.

These approaches using synthetic complexes, however, have several disadvantages as practical gene delivery tools. For example, the complex might be insoluble and heterogeneous in size, and the degree of the compaction is generally affected by salt concentration. Technical restriction to make a small complex may also limit the size of a gene to be delivered. In addition, current non-viral vector cannot be supplied as a product ready for use, because the complex containing DNA is unstable and should be prepared just before use. This is a big obstacle in consideration of commercial supply of the vector. Moreover, harsh procedures required for purifying bacterial plasmid DNA from impurities, such as alkaline-lysis method, hot phenol method, ethidium bromide/cesium chloride ultracentrifugation and chromatography, may damage the recovered DNA.

Recently, it was reported that the intrinsic membrane-penetrating activity of HIV TAT protein could be applied to the intracellular delivery of various substances (WO94/04686). It is established that a specific region of TAT protein consisting the amino acid residues, LGISYGRKKRRQR-RRPPQ (SEQ ID NO: 1), is essential for transport into cells (Vives E. et al. J. Biol. Chem. 272:16010–16017 (1997)). In this prior art, this segment was linked to various proteins and double-stranded nucleic acids to assist their delivery across the cell membrane. However, this technology can be applied only to the delivery of small piece of nucleic acid that can regulate the expression of endogenous genes through competitive inhibition, and the enhancement of the delivery of DNA fragments large enough to contain intact exogenous genes has never been established in this system.

Capsid proteins of animal viruses, such as adenovirus and SV40, contain intrinsic NLS, which is implicated in the active nuclear transport of viral genome in the early phase of infection (Greberand U. F. and Kasamatsu I. Trends Cell Biol. 16:189–195 (1996)). In addition, SV40 particle with 50 nm in diameters was suggested to be transported into the nucleus as an intact particle (HumMeler K. et al. J. Virol. 6:87–93 (1970)). Another transport system in which an exogenous gene is packaged in the capsid MS-2 phage was also reported (Published Japanese Translation of International Patent Application No. Hei 7-508168). However, no reproducible system has been established in which the intracellular delivery of a large fragment of DNA is facilitated by NLS.

To overcome these problems, the present inventors previously established a novel transport system utilizing phage particles which displays NLS peptide on their head (WO98/06828). In this system, DNA fragments were encapsulated in the phage head and were transported into the nucleus efficiently. As a consequence, expression of encapsulated genes was stimulated significantly. However, the phage particles have to be delivered into the cytoplasm by microinjection for efficient nuclear transport, because NLS could not assist the penetration of nucleic acids across the cell membrane by itself.

Incorporation of a ligand to cell surface receptors into the gene transfer vehicles is another approach for improving the efficiency. The adsorption and uptake of the phage particles by cells can be improved when a binding ligand was displayed on the tail of lambda phage (WO96/21007). However, this approach could not improve the efficiency to transport DNA into the nucleus. In case of the recombinant lambda phage displaying the cell surface ligand (RGD peptide) on the tail, the efficiency of gene transfer is not improved significantly (Dunn I. S. Biochimie 78:856–861 (1996)). In order to overcome this low efficiency, dual-display phage, with cell surface ligand on the head and with NLS on the tail, was reported (WO98/05344). However, it is still unknown whether these displayed peptides can actually improve the efficiency of gene delivery. Furthermore, complex recombinant phage such as the dual-display phage has the difficulties in the large-scale production.

Application of an insect protein called Antennapedia to the delivery of nucleic acid is also reported (Trends Cell Biol. 8:84–87 (1998)). According to this report, various substrates such as proteins and DNA can be delivered into cells and then into the nucleus by conjugated chemically or genetically with Antennapedia protein. However, this method is not sufficient for delivering the genes, because the maximum size of the substrate is limited (less than 55 nucleotides for DNA and 100 amino acid residues for protein). Other proteins such as lactoferrin (Nature 373:721–724 (1995)), herpes virus VP22 protein (Cell 88:223–233 (1997)), and fibroblast growth factor-2 (Bioessays 17:39–44 (1995)), are also reported to have the similar function as the Antennapedia protein. However, all of these proteins have a limited capacity in gene delivery as Antennapedia when conjugated to the cargo by reported procedure.

Anti-DNA antibody, detected frequently in the serum of the patient with autoimmune disease, is also known to penetrate cell membrane and to move into the nucleus. A peptide consisting of CDR2 and CDR3 domains of supervariable region of one of the clones of anti-DNA antibody was demonstrate to transport exogenous substrate such as hapten and polynucleotides to the cell nucleus (Proc. Natl. Acad. Sci. U.S.A. 95:5601–5606 (1998)). This system is claimed to be more effective for delivering huge macromolecules than those reported previously, but it still seems to be difficult to deliver DNA larger than 10 kilo base pairs because of the difficulty in the preparation of delivery complex. In addition, disadvantages common to the current non-viral vectors still remains in this system. For example, the anti-DNA peptide has to be mixed with DNA just before use, and optimal condition for the complex formation is restricted so strictly that the complex may precipitate at higher concentration.

DISCLOSURE OF THE INVENTION

An objective of the present invention is to provide a novel system for delivering extracellular substances into the nucleus highly efficiently. Specifically, it provides a novel technique utilizing recombinant bacteriophage to produce the particles encapsulating a large fragment of DNA in large scale, which enable to improve the efficiency of DNA transport at each steps of gene delivery, including penetration of the cell membrane and the nuclear membrane.

The present inventors noted the feature of TAT protein of human immunodeficiency virus that this protein could penetrate the cell membrane and the nuclear membrane by its intrinsic activity, and succeeded to develop an improved non-viral vector by employing the recombinant phage displaying a part of this bi-functional protein.

Thus, the present invention provides:

[1] a phage comprising, as a component of the head of said phage, a protein having both nuclear translocation and cell adhesion activities, or the head of said phage;

[2] the phage of [1], wherein said protein is TAT protein of HIV or its transfer active domain, or the head of said phage;

[3] the phage of [2], wherein said transfer active domain is a peptide comprising the amino acid sequence set forth in SEQ ID NO: 1, or the head of said phage;

[4] the phage of [1], wherein said phage is lambda phage, or the head of said phage;

[5] the phage of [1], wherein said protein is fused with a phage head protein, or the head of said phage;

[6] the phage of [5], wherein said phage head protein is D protein of lambda phage, or the head of said phage;

[7] a fusion protein between a protein having both nuclear translocation and cell adhesion activities and a protein that composes phage head;

[8] the fusion protein of [7], wherein said protein having both nuclear translocation and cell adhesion activities comprises the amino acid sequence set forth in SEQ ID NO: 1;

[9] the fusion protein of [7], wherein said phage is lambda phage;

[10] the fusion protein of [7], wherein said protein that composes phage head is D protein of lambda phage;

[11] A DNA fragment encoding the fusion protein of any one of [7] to [10];

[12] a vector comprising the DNA of [11];

[13] a bacterial host carrying the vector of [12];

[14] the bacterial host of [13], wherein said host is *E. coli*;

[15] a kit for cell transfection comprising (a) the bacterial host of [13] or [14], and (b) a phage comprising the head protein that is comprised in the fusion protein to be expressed in said bacterial host, wherein said phage is not capable of expressing the head protein in said bacterial host;

[16] the kit of [15], wherein said phage is lambda phage;

[17] the kit of [16], wherein said head protein is D protein of lambda phage;

[18] a method for transporting a substance from the outside of a desired cell to the nucleus of said desired cell, said method comprising (a) packaging said substance into the head of the phage of [1], and (b) exposing said phage or the head thereof to said desired cell;

[19] the method of [18], wherein said substance is a gene;

[20] the method of [19], wherein said method further comprises (c) expressing said gene in said cell;

[21] the method of [18], wherein said phage is lambda phage;

[22] the method of [18], wherein said cell is a mammalian cell;

[23] a pharmaceutical composition comprising the phage of [1] in which a component required for treatment is packaged or the head of said phage; and

[24] the pharmaceutical composition of [23], wherein said component is an expressively packaged gene and wherein said phage has cell adhesion activity toward a cell in which the gene is to be expressed.

Bacteriophage like lambda phage can package a genetic substance as large as the phage genome (31×106 to 38×106 dalton) in their capsid with 55 nm in diameter. This characteristic is advantageous because large fragment of DNA has to be packaged compactly as small as 40 nm, the diameter of a nuclear pore for nuclear transport. In addition, the DNA encapsulated in the capsid is protected from attack of DNase during purification from bacteria and even after introduced into the cells. These characteristics make the lambda phage a desirable carrier of exogenous genes to be delivered. The present inventors found that employment of the recombinant phage displaying a part of the bi-functional TAT protein as a vector could overcome all the barriers of DNA delivery 4enetration of the cell membrane and transport across the nuclear membrane), and this observation accomplished the present invention.

Previous patent application by the present inventors (WO98/06828) disclosed the basic procedures composing the present invention. Namely, the present invention can be implemented by using a protein with the activities of nuclear translocation and cell adhesion, instead of nuclear localization signal (NLS), which was utilized to modify the phage head in the previous application. The procedures are specifically described as follows.

A fusion protein comprising lambda phage head (D protein) and the protein with both nuclear translocation and cell adhesion activities, claimed in this invention, is expressed in host *E. coli* cells using an appropriate vector. The host cells are lysogenized with a mutant lambda phage deficient in head formation ("D amber phage" hereinafter). A gene to be transported is incorporated into the genome of D amber phage so that the gene can be expressed in target cells. Recombinant lambda phage, claimed in this invention, is prepared by inducing the replication of D amber phage and the production of fusion D protein in single bacterial cells. These procedures are also described in detail in the previous patent application WO98/06828.

In this prior art, D amber phage is constructed based on lambda Dam15. As another source of D amber phage, lysogenic *E. coli* BHB2690 (lambda Dam15 b2 red3 imm434cIts Sam7), which is available as ATCC 35132, can be used. The Left Arm 17050 bp and the Middle fragment 1510 bp of lambda Dam15 can be prepared from D amber phage carried in *E. coli* BHB2690.

The phage prepared as described as above displays the D protein with the activity of nuclear translocation and cell adhesion, and encapsulates a gene to be transported into the nucleus of target cells. Once the phage is exposed to cells, it binds to and penetrates into the cells, then moves into the nucleus through its nuclear localization activity. Diameter of the phage head is approximately 55 nm, the size close to that of SV40 virus particle (50 nm), which is thought to be sufficiently small for transporting their genome DNA into the nucleus through nuclear pores. The present invention enables in vivo gene transfer without the aid of other agents because the intrinsic activity of the recombinant phage accomplishes efficient delivery of DNA, from the outside of the cells to the nucleus. In this invention, the head of the recombinant phage is an essential and sufficient structure for both cell targeting and DNA encapsulation. Therefore, the tail of the phage, which is naturally required for infection to host bacterium, is dispensable for this invention. Specific embodiments of the present invention are described in the followings.

The present invention relates to the techniques for packaging a foreign substance in the phage head modified with a bi-functional protein that carries both nuclear translocation and cell binding activities (described as a bi-functional protein hereinafter). It also relates to the techniques for delivering the phage into a desired cell and for transporting a phage particle encapsulating exogenous substance into the nucleus of target cells.

For accomplishing the purpose of this invention, one may use any kind of bi-functional proteins, as long as they carry both nuclear translocation and cell binding activities. For instance, TAT protein of HIV is a favorable bi-functional protein for transporting lambda phage particle. However, other proteins may used instead of TAT protein, such as a variable region of anti-DNA antibody, Drosophila antennapedia protein, lactoferrin (Nature 373:721–724 (1995)), herpes virus VP22 protein (Cell 88:223–233 (1997)), polyomavirus VP1 protein; polyomavirus VP2 protein, polyomavirus VP3 protein, adeno associated virus Cap protein, and fibroblast growth factor-2 (Bioessays 17:39–44 (1995)). As for TAT protein, it is established that the sequence shown in SEQ ID NO: 1 is a domain that confers both of the functions described above (Vives E. et al. J. Biol. Chem. 272:16010–16017 (1997)).

In this invention, we define a region essential for nuclear translocation and cell adhesion activities, or a region comprising this essential region as a part of it, as a transfer active domain. Therefore, when TAT protein is used as a bi-functional protein essential for the present invention, it is desirable to design a hybrid protein comprising the sequence of SEQ ID NO: 1.

Other proteins as described above, that is, a variable region of anti-DNA antibody, lactoferrin, herpes virus VP22 protein, polyomavirus VP 1 protein, polyomavirus VP2 protein, polyomavirus VP3 protein, adeno associated virus Cap protein, fibroblast growth factor-2, and so on, may also be utilized by first identifying the transfer active domain and then modifying phage with the domain. For instance, in antennapedia, which is involved in Drosophila differentiation, the peptide corresponding to the amino acid sequence from the positions 43 to 58 (RQIKIWFQNRRMKWKK (SEQ ID NO: 4); helix 3) within the homeodomain is identified as a transfer active domain. Thus, a protein comprising this sequence can be used as a bi-functional protein of the invention. In the variable region of anti-DNA antibody, the sequence corresponding to the supervariable region, CDR2+CDR3, (VAYISRGGVSTYYSDTVKGRFTRQKYNKRA (SEQ ID NO: 5)) is reported to be a transfer active domain. A protein comprising the sequence may also be utilized as a bi-functional protein of the invention.

A phage used in the present invention is not restricted to lambda phage as long as it is capable of packaging a foreign substance in its head; lambda phage and M13 phage can be used. Also, utilized as a carrier in the invention may be P1 phage, P22 phage, T1 phage, T2 phage, T3 phage, T4 phage, T5 phage, T6 phage, T7 phage, P2 phage, P4 phage, Mu phage, Pm2 phage, N4 phage, SP01 phage, PBS1 phage, PBS2 phage, etc.

For preparing phage having a protein with both nuclear translocation and cell adhesion activities as a component of its head, a variety of methods can be used. One preferred embodiment is use of recombinant DNA technology. For instance, a DNA encoding the protein with both nuclear translocation and cell adhesion activities and a gene encoding a phage head protein are ligated and cloned into a vector. The resulting fusion protein is expressed in bacterial host cells. Thereafter, a mutant phage that is incapable of expressing the head protein is amplified in the host cells, and the phage head is formed. In this system, any gene can be packaged into phage by inserting the gene into phage DNA. Thus, the gene is recovered as a component of phage particle, which can be recovered from *E. coli* by centrifugation. Because the recovering procedure does not require any harsh purification step, the damage to the gene can be avoided.

Furthermore, the present invention provides a kit for packaging foreign gene into a phage, the kit comprising the above bacterial host cells and a phage vector having cloning sites for insertion of a gene. Herein, the phage head protein is not restricted; gpD protein and gpE protein in case of lambda phage and gene 3 protein in case of M13 phage can be used.

Also, a vector in this embodiment (for expression of a fusion protein composing phage head) is not restricted but a variety of vectors may be used. Bacterial host cells are not restricted either as long as the phage to be used can be replicated. For instance, in use of lambda phage, various strains of *E. coli* in which the phage can proliferate may be used. Herein, DNA encoding the amino acid sequence of a protein having both nuclear translocation and cell adhesion activities and a gene encoding the phage head protein may be directly linked, but may also be linked through spacer nucleotides.

Alternatively, a chemical method may be used to conjugate the above bi-functional protein and the phage head protein. The proteins may be directly conjugated, but may also be linked through crosslinkers or spacer peptides.

A phage of the invention is transfected into cells while packaging a foreign substance in itself. For packaging, the method of Ishiura et al. (Gene 82:281–289 (1989)), or that of Sternberg et al. (Published Japanese Translation of International Patent Application No. Sho 59-500042) may be used. A foreign substance may be a gene, gene fragment, ribozyme, antisense gene, or any other substance that is desired to function in the nucleus. In gene therapy, for instance, a normal gene that is the counterpart of a deficient gene may be used. In case of functional analysis of a particular gene, an antisense DNA of the gene can be utilized. Furthermore, in case of creation of transgenic animals, a gene involved in a desired phenotype may be introduced.

The present invention enables packaging a large DNA fragment such as genes containing the upstream flanking regions. For instance, the present invention, using a phage as a carrier, enables packaging a gigantic gene as long as 50 kb. Specifically, the whole genome of an animal virus or multiple genes involved in a series of functions can be integrated. As the recombinant lambda phage particle also enables packaging a cosmid vector, it is possible to apply the method of the present invention to a gigantic gene such as dystrophin cDNA (13.8 kb). Such a long DNA can be packaged into the size that permits efficient nuclear translocation by the intrinsic machinery of the phage.

If the phage packaging a foreign substance based on the present invention is administered in vivo, it translocates to the nucleus without any aid of physical methods. Thus, nuclear translocation is achieved by simply exposing the phages to target cells. Here, exposure of phage to cells is defined as to incubate phages and cells for a certain time without any artificial and physical treatment that aims at substance transport into the cell. This is in contrast to previous methods, in which phage was modified with NLS alone, supporting no function to help cellular incorporation, and thus physical methods such as microinjection were used. Thus, the phage (or its head) of the present invention can be utilized to develop a pharmaceutical composition that is aimed at applications in vivo or ex vivo. For instance, it is possible to perform a novel approach like transporting the whole genome of a virus having cytotoxicity, such as adenovirus (the genome size is approximately 36 kb), to cancer cells and expressing it in those cells. The invention can also be applied in an approach such as expressing multiple lymphokines that are capable of activating the immune system in a single cell. For instance, genes encoding lymphokines such as interleukine-2, interleukine-6, granule colony stimulating factor, and so on are ligated downstream of an appropriate promoter for expression and packaged in the phage of the invention. The resulting phages are exposed to cells such as lymphocytes, which are returned to a body (ex vivo), and thereby, cells producing multiple lymphokines that activate the immune system can be introduced into the body.

As the case that human being has antibodies against phages is usually rare, it is likely that the administered phages is not rapidly eliminated but stays in the body, adheres to target cells, and is finally incorporated therein. In the above-described embodiment in which adenovirus is packaged, the virus is transported to the inside of target cells while its antigenicity is masked. If a gene is packaged in the phage of the invention, the gene is transported into the nucleus of adhered cells, where it is expressed efficiently. For in vivo application, phage may be directly injected into a target organ, or intravenously injected into the vessel that is supplying blood to the target organ, and then maintained at high concentration for a certain time within the blood vessels of the organ by controlling blood flow.

In an in vivo administration, the phage is generally prepared at a concentration of $10^{10}$ to $10^{14}$ PFU/ml. If its concentration is far below this range, the titer of phage is probably insufficient, while if it exceeds the range, it may cause problems such as precipitation. However, the concentration range is not definitive; for instance, if the phage can deliver the gene quite efficiently into particular target cells, or in case where only a few amount of phage can achieve sufficient effect, a lower concentration may be used in practice. More specifically, preliminary experiments should be performed to obtain MOI (multiplicity of infection) and to determine the most effective concentration, because infectivity can change depending on the combination between phages and target cells. Because the administration method itself also limits the applicable volume of solution, the phage concentration and the solution volume must be determined by taking all these conditions into account. For instance, the maximal volume used for direct injection into human organs, even such a large organ as the liver, is generally around 100 ml.

The phage of the present invention can be commercially supplied as a pharmaceutical composition aimed at in vivo administration. The pharmaceutical composition may be obtained by suspending the phage at required concentration in an appropriate buffer that is biologically acceptable. The solvent generally used is SM (10 mM Tris-HCl (pH 7.4), 10 mM MgSO$_4$, 0.1 M NaCl, 0.01% gelatin) for liquid, and 3XD Medium or LB+15% glycerol for lyophilized products (Hendrix R. Lambda II, Cold Spring Harbor Laboratory (1983)). The products can be distributed in the form of solution or in a lyophilized state, and preferably at low temperature (4° C.). The composition may be supplemented with glycerol, serum albumin, gelatin, putrescine, and so on for phage stabilization. It may also be mixed with fluorescent dye or a variety of contrast media to aid manipulation of in vivo administration. It is convenient to add contrast medium for X-ray or MRI, which allows visualizing the conditions of injection.

Target cells, which are to be transfected with a phage packaging a foreign substance, may not be restricted to any particular kind, but a variety of cells may be used depending on purposes. However, be the combination of target cells and the above-described bi-functional protein is critical because the phages are modified with the protein having nuclear translocation and cell adhesion activities. The cell adhesion activity of the bi-functional protein used herein for modifying phages must be directed to target cells. TAT protein of HIV is a suitable bi-functional protein for targeting human cells. Furthermore, the phage of the present invention can be applied not only to a particular organ, but also to lesion such as those in tumors, arteriosclerosis, and the like.

BEST MODE FOR CARRYING OUT THE INVENTION

The present invention is illustrated in detail below with reference to examples, but is not to be construed as being limited thereto.

EXAMPLE 1

Construction of TAT Peptide-gpD Fusion Protein Expression Vector cDNA encoding gpD protein, one of proteins composing lambda phage head, was cloned by PCR using wild-type lambda phage as a template. Specifically, according to the method disclosed in WO98/06828, the previous patent application of the present inventors, a vector named pTrcHisA-gpD was constructed. After the DNA sequence was verified by cycle sequencing, the vector was introduced into *E. coli* TOP10 (Grant S. G. N. et al. Proc. Natl. Acad. Sci. U.S.A. 87:4645–4649 (1990)), and gpD protein was overexpressed in the bacteria. Expression of the protein was examined by SDS-PAGE. As a result, a strong band was detected at the position of 11.6 kDa, the molecular weight of the protein, in the lane for the sample obtained 6 hr after induction with 1 mM IPTG.

Figure 1:
FIG. 1 schematically shows the structure of HIV-TAT-gpD fusion protein (SEQ ID NO: 6).

Next, the fusion protein between TAT peptide and gpD was expressed in *E. coli*. A region of TAT peptide corresponding to the amino acid sequence from the positions 43 to 60 (LGISYGRKKRRQRRRPPQ (SEQ ID NO: 1); FIG. 1), which was known to be able to permeate the cell membrane and translocate to the nucleus (Vives E. et al. J. Biol. Chem. 272:16010–16017 (1997)), was used. Oligonucleotides corresponding to the sequence was synthesized, and subdloned into the NcoI site of the pTrcHisA-gpD vector to construct pTrc-TAT-gpD. After the DNA sequence was verified by cycle sequencing, the vector was introduced into *E. coli* TOP10, and a fusion protein between NLS and gpD protein was overexpressed in the bacteria. Expression of the protein was examined by SDS-PAGE. As a result, a strong band was detected at the position of the expected molecular weight of the protein in the lane for the sample obtained 6 hr after induction with 1 mM IPTG.

EXAMPLE 2

Construction of TAT-peptide-presenting Lambda Phage in Which Marker Gene is Cloned

Figure 2:
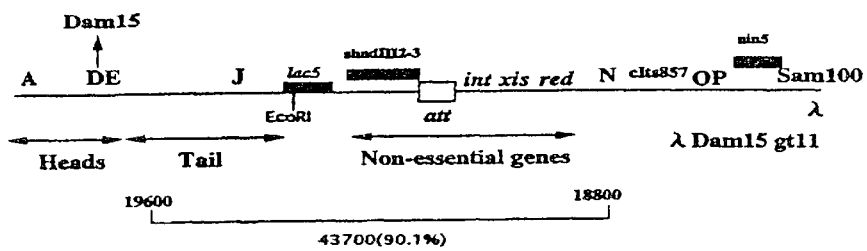
FIG. 2 shows construction process of TAT-peptide-presenting lambda phage in which a marker gene is cloned.
Figure 2:
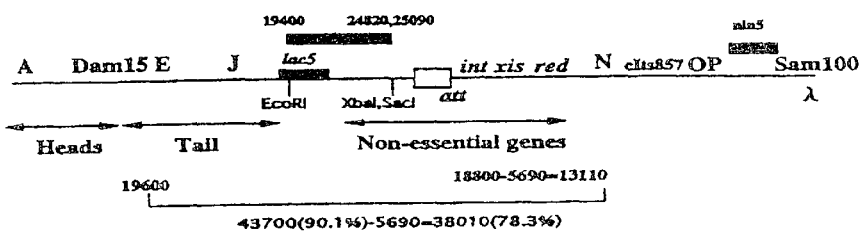
Figure 2:
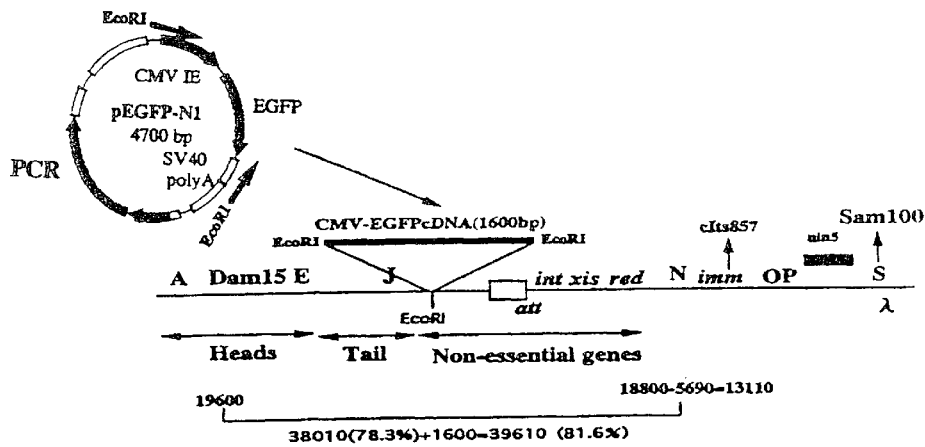
Figure 2:
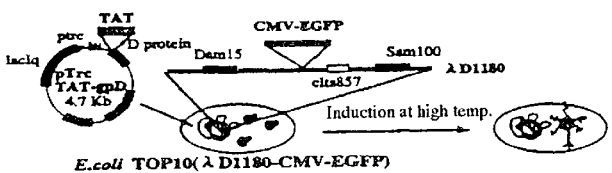

*E. coli* TOP10 (λD1180-CMV-EGFP) was prepared according to the scheme shown in FIG. 2.

First, an amber mutation was introduced into the D gene of λgt11. Specifically, λgt11 (Stratagene) was digested with KpnI to obtain Right Arm 25410 bp, and λDam15 (a gift from Iguchi H., Kyoto University) was digested with KpnI to obtain Left Arm 17050 bp, and Middle fragment 1510 bp. These three fragments were ligated, packaged using Giga-packIII gold packaging extract (Stratagene), and infected into *E. coli* Y1088 to make plaques formed. Phages from each plaque were further infected into *E. coli* C600 (supE) (Stratagene) and TOP10 (supo) (Invitrogen), and phages that formed plaque in the former bacteria but failed in the latter were obtained (λDam15-gt 1). This is based on the principle that C600 (supE) can complement Dam15, but TOP10 (supo) cannot, and thus, phages fail to be packaged in the bacteria.

Next, λD1180, which has 80% genome size of that of λ Dam15-gt11, was constructed. Specifically, λDam15-gt11 was digested with EcoRI and SacI, and Left Arm 19600 bp and Right Arm 13110 bp were prepared. The two fragments were ligated with EcoRI-SacI linker (5'-AATTCGGCGGCCGCGAGCT-3'/5'-CGCGGCCGCCG-3' (SEQ ID NOS: 7 and 8)), and λD1180, 38010 bp in total, was constructed. CMV-EGFP-SV40 polyA (1600 bp), a unit for gene expression in mammalian cells, was prepared by PCR. Specifically, PCR was performed using pEGFP-N 1 (Clontech) as a template with primers, 5'-GGGCGTGAATTCTAGTTATTAATAGTAA-3' (SEQ ID NO: 2; having an EcoRI site in the sequence from the positions 7 to 12 at the 5'-end side) and 5'-GGGCGGAATTCCGCTTACAATTTACGCCTTAAG-3' (SEQ ID NO: 3; having an EcoRI site in the sequence from the positions 7 to 12 at the 5'-end side). PCR was performed in 50 µl of 1×ThermoPol buffer (10 mM KCl, 2 mM MgSO$_4$, 10 mM (NH$_4$)$_2$SO$_4$, 20 mM Tris-HCl (pH 8.8), 0.1% Triton X-100; New England Biolabs) containing 35 ng template, 200 HM primers, 500 nM dNTP, and 2 U Vent DNA polymerase (New England Biolabs) with a single cycle of heat denaturation at 94° C. for 5 min, followed by 25 cycles of heat denaturation at 94° C. for 30 sec, annealing at 50° C. for 1 min, and extension at 72° C. for 2 min. The amplified DNA fragments were digested with EcoRI and subcloned into the EcoRI site of λD1180 to construct λD1180-CMV-EGFP. Furthermore, this phage was lysogenized into *E. coli* TOP10 to obtain TOP10 (λD1180-CMV-EGFP). Because the phage harbors D amber mutation, it does not express gpD in the host cells without suppressor+RNA, and usually its head is composed of gpE alone (two proteins, gpD and gpE, compose wild type lambda phage head). Such a phage expressing gpE alone is extremely sensitive to EDTA. Also, cI encoded by the phage, which is a repressor of the phage, is temperature sensitive. Thus, by treatment at 42° C. for 15 min, the repressor is released, and the phage becomes competent for bacteriolysis. On the other hand, if TAT-gpD fusion protein is expressed in the bacteria and incorporated into the phage induced by heat shock, the resulting phage will be EDTA resistant. Accordingly, the phages were prepared on 4-ml scale, treated with 10 mM EDTA, and then infected into *E. coli* LE392, and the titer was measured. As shown in Table 1, it was confirmed that the recombinant phages in which TAT-gpD used in Example 1 had been integrated at their head were EDTA resistant, suggesting that the structure was stabilized.

TABLE 1

Titers of lambda phages that have recombinant head protein

| Protein | Titer (PFU/ml) (analysis in *E. coli* LE392) | |
| --- | --- | --- |
| | EDTA (−) | EDTA (+) |
| — | 4.0 × 10$^9$ | 1.0 × 10$^3$ |
| gpD | 8.6 × 10$^8$ | 6.8 × 10$^8$ |
| HIV-TAT-gpD fusion protein | 1.0 × 10$^8$ | 1.0 × 10$^8$ |

EXAMPLE 3

Figure 3:
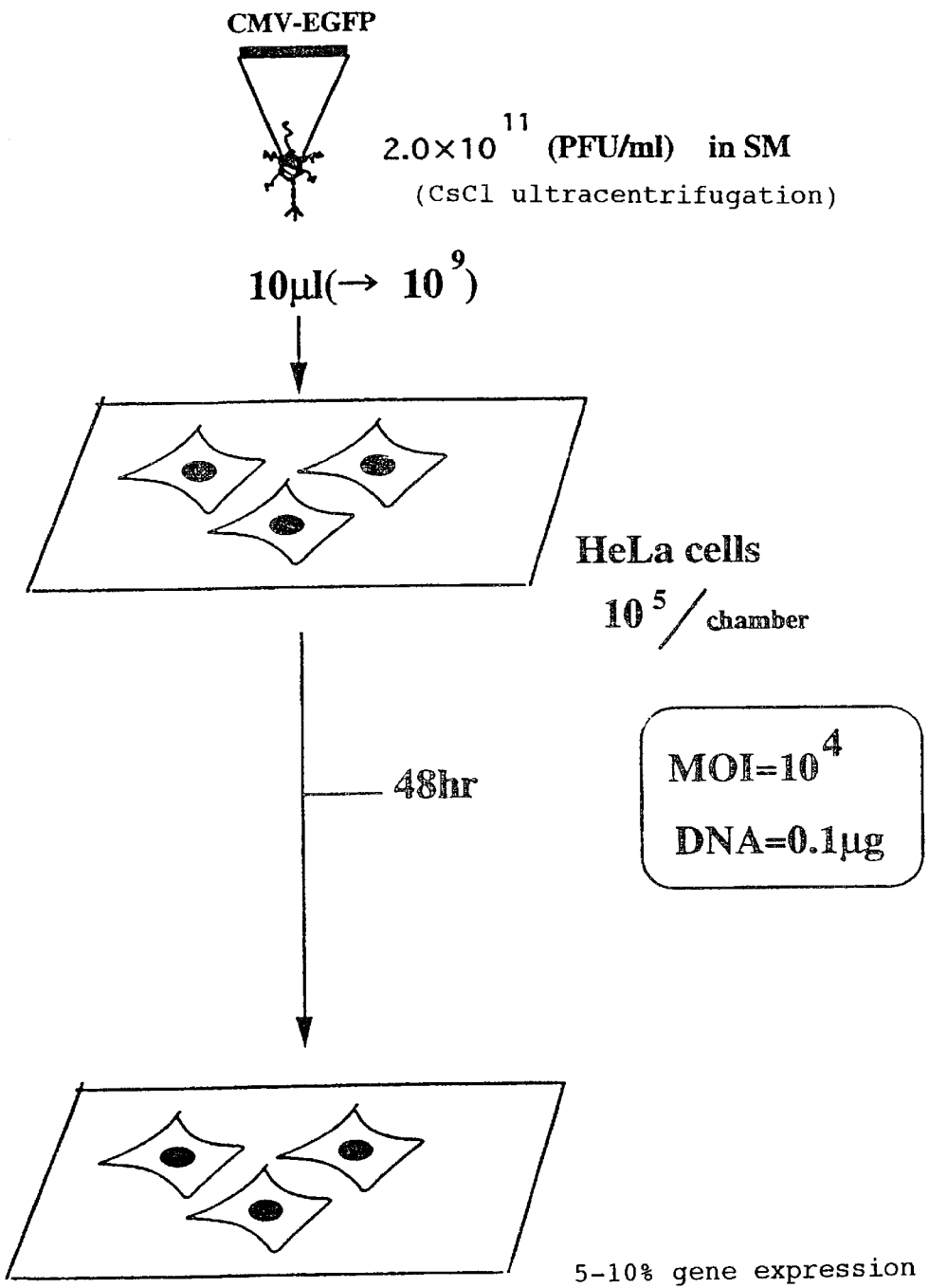
FIG. 3 schematically shows transfection procedures.

Transfection of TAT-peptide-presenting Lambda Phage (1) Preparation of Lambda Phage Particles Presenting TAT Peptide Transfection scheme is shown in FIG. 3. *E. coli* TOP10 (λD1180-CMV-EGFP) transformed with pTrc-TAT-gpD was cultured at 32° C. in LB medium containing 10 mM Mg. After reaching log phase (2×10$^8$ cells/ml), the culture was shaken at 42° C. for 15 min to induce phage production. Then, expression the fusion protein was induced with 0.5 mM IPTG. After shaken at 38° C. for 2.5 hr, the bacteria were collected by centrifugation at 5000 rpm for 10 min and resuspended in SM buffer (0.1 M NaCl, 8 mM MgSO$_4$, 50 mM Tris-HCl (pH 7.5)). The concentrated cells were lysed by adding chloroform prewarmed at 37° C. and stirring. Furthermore, DNase was added, and centrifugation was performed at 8000 rpm for 30 min to remove insoluble materials. The supernatant was further centrifuged at 23000 rpm for 1 hr, and the phages precipitated were resuspended in SM buffer. Collected phage particles were purified by centrifugation on cesium chloride density gradient. Particles were resuspended in SM buffer to have TAT-peptide-presenting lambda phage at 1×10$^{11}$ PFU/ml.

(2) Transfection and Detection of Gene Expression

Figure 4:
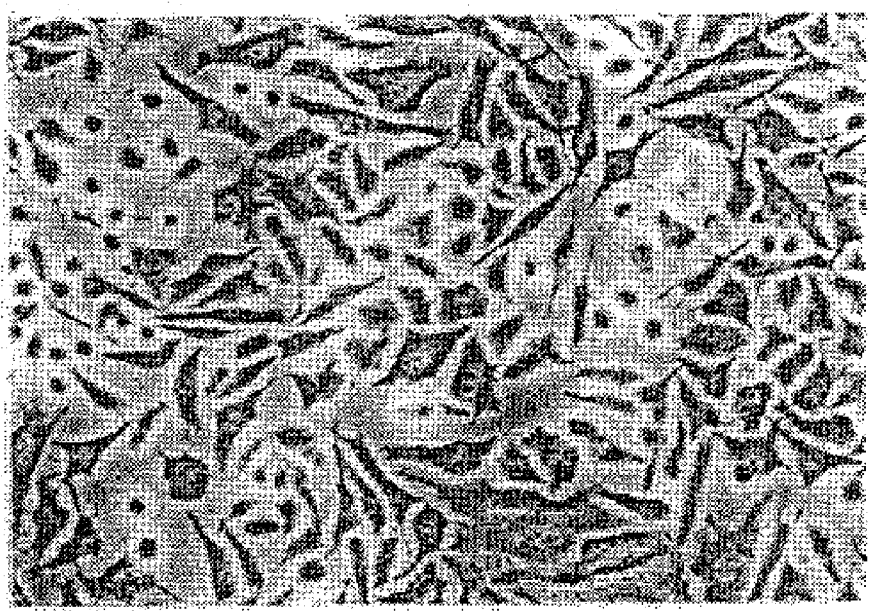
FIG. 4 shows micrographs of HeLa cells treated with the phages of the present invention (48 hr after transfection). The upper panel shows a phase contrast micrograph (bright field), and the lower panel shows a fluorescence micrograph of the same sample.
Figure 4:
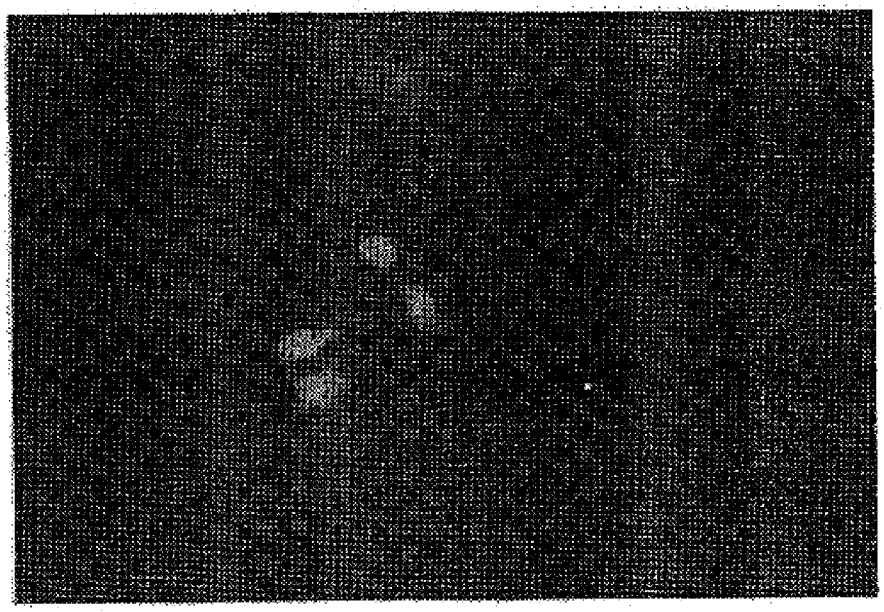
Figure 5:
FIG. 5 shows micrographs of control HeLa cells treated with wild-type phages (48 hr after transfection). The upper panel shows a phase contrast micrograph (bright field), and the lower panel shows a fluorescence micrograph of the same sample.
Figure 5:
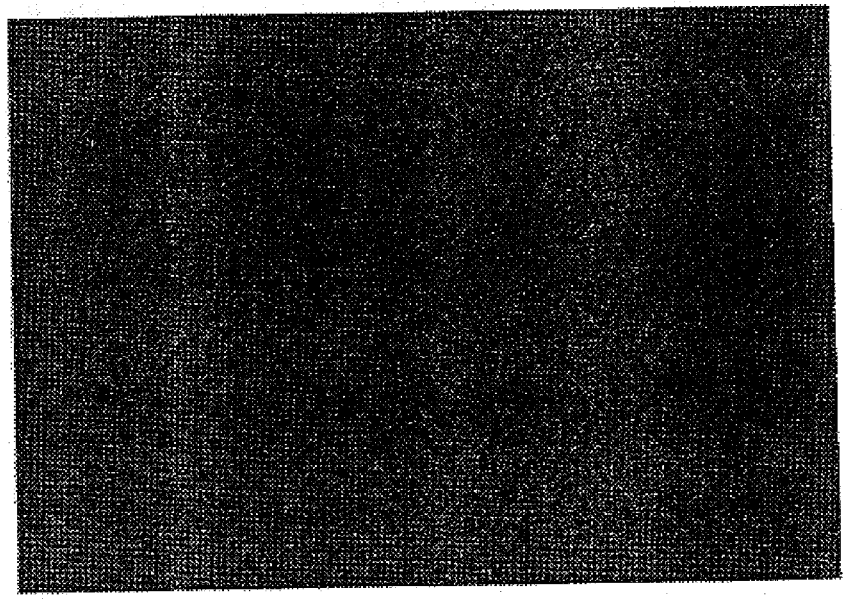

HeLa cells (GIBCO-BRL) in MEM media containing 10% bovine calf serum, COS-7 cells (GIBCO-BRL) in DMEM media containing 10% bovine calf serum, and NIH 3T3 cells (GIBCO-BRL) in DMEM media containing 10% fetal bovine serum were cultured and plated at 1×10$^5$ cells/chamber (Falcon Culture Slide 4101; 50% confluency). On the next day, TAT-peptide-presenting lambda phage (1×10$^{11}$ PFU/ml) was added to the cells at 10 µl/chamber to make MOI=10000, and the cells were cultured for 48 hr. Expression of EGFP gene was detected by fluorescence microscopy. Microphotographs of cells treated with the phages of the present invention and those of control cells treated with wild-type phages are shown in FIG. 4 and FIG. 5, respectively. About 10% of the cells exposed to the phages of the invention were positive for gene expression (FIG. 4). Similar results were obtained in COS-7 and NIH 3T3 cells. Effect of serum on gene expression was examined by exposing the phages to cells in the absence or presence of serum for 5 hr, then changing medium and incubating for 48 hr. There was no significant difference in expression efficiency between the two conditions.

EXAMPLE 4

Application to Luciferase Gene (1) Construction of λD1180-CMV-luc, in Which Luciferase Gene is Inserted The λD1180-CMV-luc phage was constructed, in which luciferase gene was inserted instead of EGFP, whose expression was confirmed in Example 3. Specifically, firefly luciferase cDNA fragment was excised from the pGL3-Basic vector (Promega) by digestion with HindIII and XbaI, and its ends were blunted. The fragment was ligated into the pCMV-β vector (Clontech) that had been digested with NotI and blunted, and thus, pCMV-luc was constructed. Then, pCMV-luc was digested with SalI and EcoRI to excise a gene expression unit of CMV-luc-SV40 polyA. This unit was blunted and ligated into pCR Blunt (Invitrogen) to construct pCR-CMV-luc. pCR-CMV-luc was digested with EcoRI, and subdloned into the EcoRI site of λD1180 to construct λD1180-CMV-luc. Furthermore, the phage was lysogenized into *E. coli* TOP10, and TOP10 (λD1180-CMV-luc) was constructed. A foreign gene cloned in the phage is approximately 2100 bp, the size corresponding to about 82.7% of the whole genome.

For the purpose of comparison, one control construct in which TOP10 (λD1180-CMV-luc), containing the same expression unit, was combined with SV40 large T antigen NLS-presenting lambda phage (WO98/06828) and another control construct in which TOP10 (λD1180-CMV-luc) was infected into *E. coli* LE392 (supE, supF) and was combined with wild-type phage were prepared.

(2) Expression of Luciferase Gene

Figure 6:
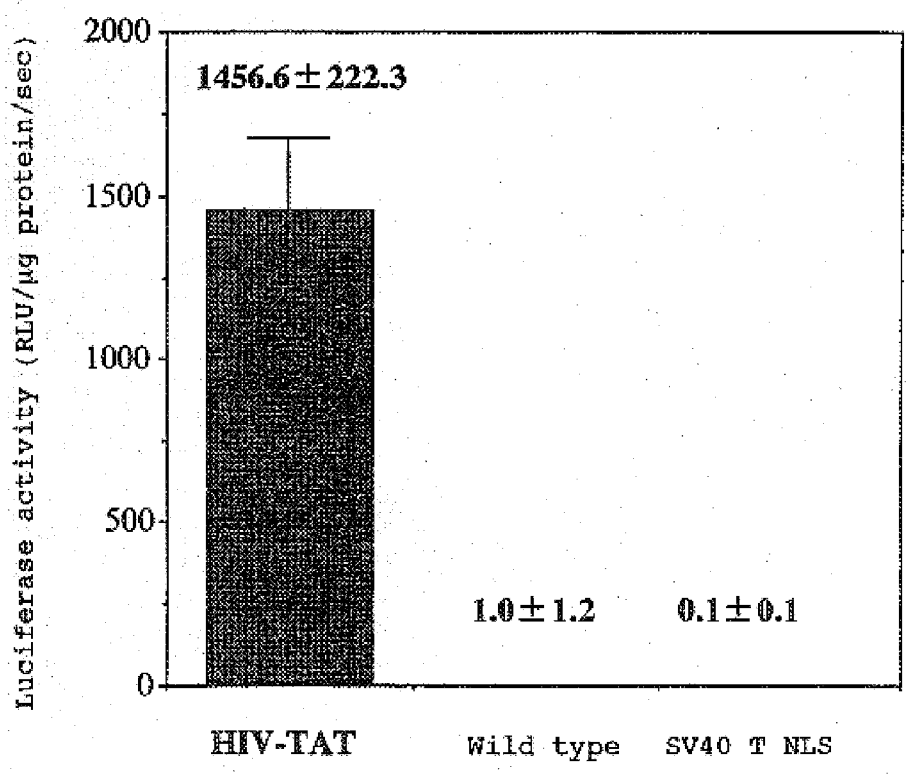
FIG. 6 shows the results of transfection using the phages of the invention in which luciferase gene is packaged. The ordinate represents luciferase activity (RLU/tg protein/sec), and the abscissa indicates phages exposed to cells.

COS-7 cells were cultured in DMEM containing 10% bovine calf serum (GIBCO-BRL), and plated at $2\times10^4$ cells/well (Corning 24-well Culture plate 25820) (50% confluency). On the next day, TAT-peptide-presenting lambda phage, SV40 large T antigen NLS-presenting lambda phage, or wild-type lambda phage ($1\times10^{10}$ PFU/ml each) was added to the cells at 10 μl/well (MOI=10000), and the cells were cultured for 48 hr. Expression of luciferase gene was detected by using the luciferase assay system (PicaGene) and a luminometer (AutoLumat LB953, Berthold). The activity was represented as relative light unit (RLU)/μg protein/sec. Experiment was performed in triplicate. The results were shown in FIG. 6. Gene expression was detected when TAT-peptide-presenting lambda phage was used, whereas no luciferase activity was detected with either SV40 large T antigen NLS-presenting lambda phage or wild-type lambda phage.

Figure 7:
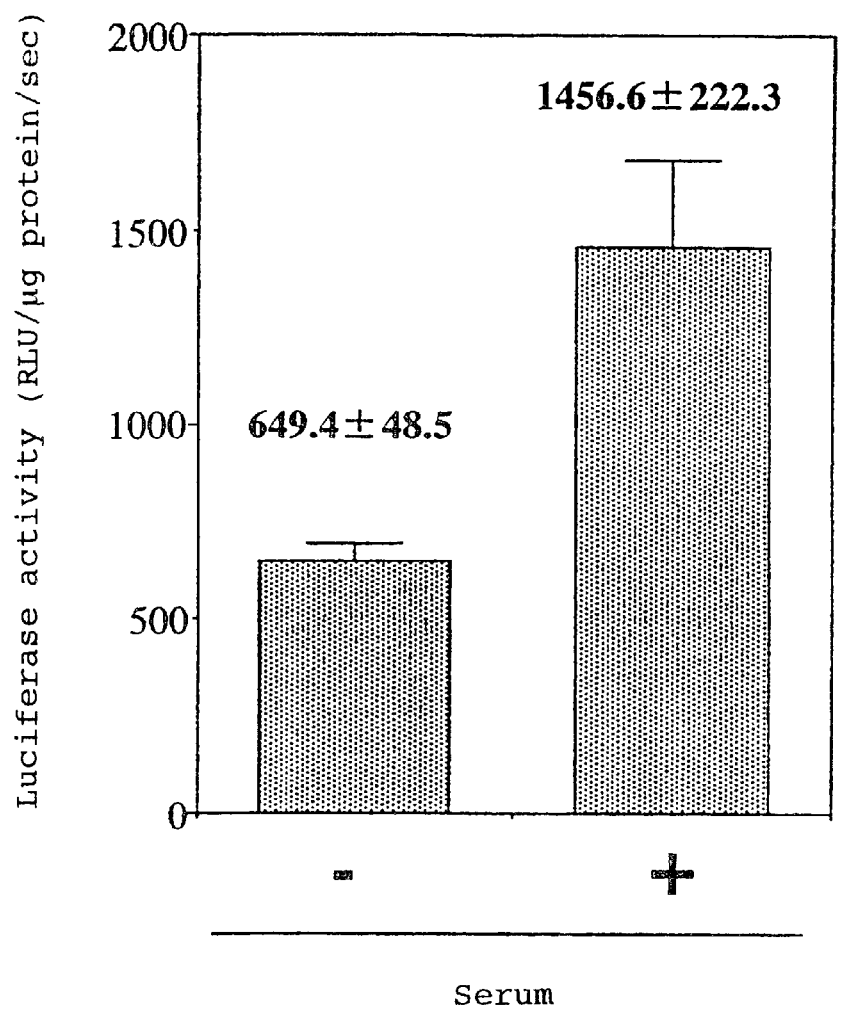
FIG. 7 shows effects of serum on the expression of luciferase gene transfected into cells by using the TAT lambda phage particles of the present invention. The ordinate represents luciferase activity (RLU/tg protein/sec), and the abscissa indicates the presence or absence of serum when the phages were exposed to cells.
Figure 8:
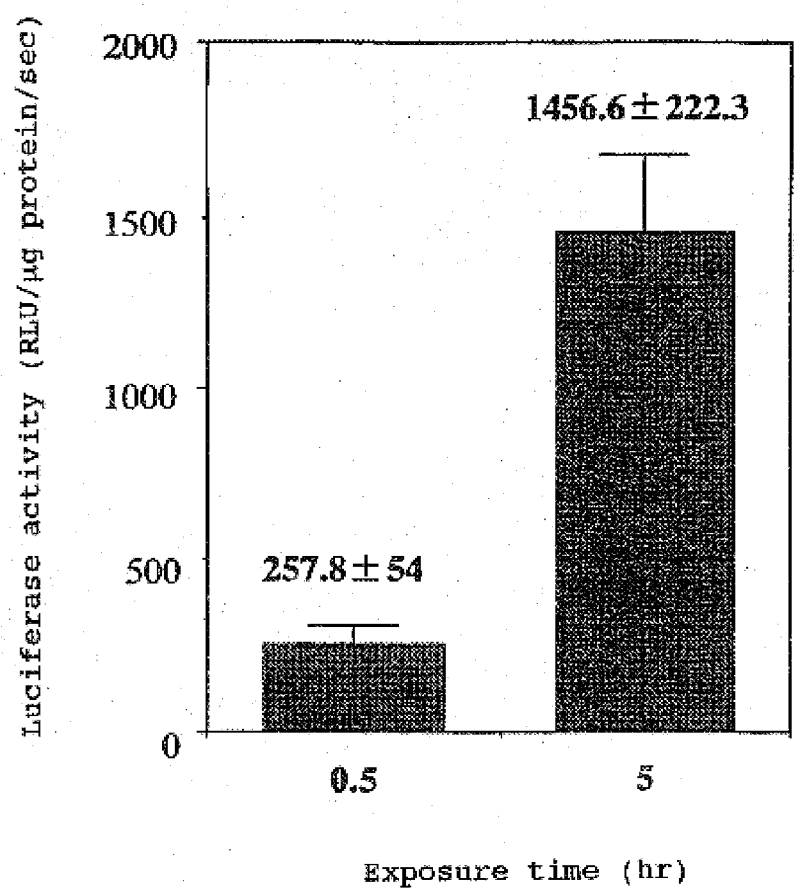
FIG. 8 shows effects of time for exposing the TAT lambda phage particles of the present invention to cells on the expression of luciferase gene transfected into the cells. The ordinate represents luciferase activity (RLU/µg protein/sec), and the abscissa indicates exposure times.

The effect of serum on luciferase gene expression was examined by exposing each kind of phages to cells for 5 hr in the absence or presence of serum, then removing the phages by medium change, and culturing the cells for 48 hr. Slightly higher expression was detected for the cells to which the phages were exposed in the presence of serum (FIG. 7). Exposure time was also examined; the phages were exposed to COS-7 cells in the presence of 10% bovine calf serum at 37° C. for 0.5 or 5 hr. Significant expression was also detected in the cells exposed for 0.5 hr, which was shorter exposure time (FIG. 8).

Industrial Applicability

The present invention provides a phage that is capable of packaging a gigantic molecule, adhering to cells, and traveling through the cell membrane to the nucleus. The phage is provided with two functions, cell adhesion and nuclear translocation activities. As the phage of the invention is capable of transporting a foreign substance to the inside of cells without any aid of physical methods, it is possible to perform its in vivo administration safely. The transfer efficiency and expression level (in case of a gene) are higher in the presence of serum. Thus, the phage has a desirable feature for in vivo application, in contrast to features of known chemical methods, in which it is almost impossible to transport substances in the presence of serum. Moreover, the phage of the invention requires only short exposure time, 0.5 hour, at 37° C. to achieve a certain level of gene transfer and expression. This suggests that gene therapy may be efficiently performed in a very short time by using the phage of the invention.

Furthermore, the phage of the invention can be prepared efficiently by using such an easy method for those skilled in the art as recombinant DNA technology and possesses high industrial applicability. Also, use of a bi-functional protein enables achieving high titer because the method only requires integration of a single protein and thus does not affect the phage structure significantly. Moreover, in one preferred embodiment of the present invention, a foreign gene that is packaged in the phage is surely expressed in target cells, implying that a novel approach can be performed in gene therapy with certainty and safety.

Use of the present method, which permits to package a gigantic molecule, makes it possible to transport a foreign gene of interest to the nucleus as a large DNA fragment containing its upstream region. Therefore, the invention is useful in a variety of fields such as better understanding of life phenomena and gene therapy.

What is claimed is:

1. A fusion protein comprising (i) a protein having both nuclear translocation and cell adhesion activities and (ii) a protein comprising lambda phage head protein, wherein said protein having both nuclear translocation and cell adhesion activities comprises the amino acid sequence set forth in SEQ ID NO: 1 and wherein said lambda phase head protein comprises D protein of lambda phage.

2. A DNA fragment encoding the fusion protein of claim 1.

3. A vector comprising the DNA of claim 2.

4. A bacterial host carrying the vector of claim 3.

5. The bacterial host of claim 4, wherein said host is *E. coli*.

6. A kit for cell transfection comprising (a) a bacterial host expressing a fusion protein comprising (i) a protein having both nuclear translocation and cell adhesion activities and comprising the amino acid sequence set forth in SEQ ID NO: 1 and (ii) a protein comprising lambda phage head protein, and (b) a lambda phage, wherein said phage is not capable of expressing said phage head protein in said bacterial host and said phage head protein comprises D protein of lambda phage.

7. A lambda phage head comprising a protein having both nuclear translocation and cell adhesion activities, wherein said protein is the TAT protein of HIV or its transfer active domain and wherein said protein is fused with D protein of lambda phage.

8. The phage head of claim 7, wherein said transfer active domain is a peptide comprising the amino acid sequence of SEQ ID NO: 1.

9. The phage head of claim 7, wherein said phage head is accompanied by its tail.

10. The phage head of claim 9, wherein said transfer active domain is a peptide comprising the amino acid sequence of SEQ ID NO: 1.

11. A method for transporting a substance from the outside of a desired cell to the nucleus of said desired cell, said method comprising (a) packaging said substance into the lambda phage head of claim 7; and (b) exposing said lambda phage head to said desired cell.

12. The method of claim 11, wherein said substance is a gene.

13. The method of claim 12, wherein said method further comprises (c) expressing said gene in said cell.

14. The method of claim 13, wherein said cell is a mammalian cell.

15. A method for transporting a substance from the outside of a desired cell to the nucleus of said desired cell, said method comprising (a) providing a fusion protein comprising (i) a protein having both nuclear translocation and cell adhesion activities and (ii) a protein comprising a lambda phage head, wherein said protein having both nuclear translocation and cell adhesion activities comprises SEQ ID NO: 1 and said phage head protein comprises D protein of lambda phage, (b) packaging said substance into a lambda phage head, and (c) exposing said lambda phage head comprising said fusion protein to said desired cell.

16. The method of claim 15, wherein said substance is a gene.

17. The method of claim 16, wherein said method further comprises (d) expressing said gene in said cell.

18. The method of claim 17, wherein said cell is a mammalian cell.

* * * * *

UNITED STATES PATENT AND TRADEMARK OFFICE
CERTIFICATE OF CORRECTION

PATENT NO. : 6,740,524 B1
DATED : May 25, 2004
INVENTOR(S) : Akuta et al.

It is certified that error appears in the above-identified patent and that said Letters Patent is hereby corrected as shown below:

Column 17,
Lines 4 and 19, replace "comprising lambda phage" with -- comprising a lambda phage --;
Line 7, replace "lambda phase" with -- lambda phage --;

Column 18,
Line 13, replace "The method of claim 13" with -- The method of claim 11 --; and
Line 30, replace "The method of claim 17" with -- The method of claim 15 --.

Signed and Sealed this

Fourteenth Day of September, 2004

JON W. DUDAS
*Director of the United States Patent and Trademark Office*

```
                        SEQUENCE LISTING

<160> NUMBER OF SEQ ID NOS: 8

<210> SEQ ID NO 1
<211> LENGTH: 18
<212> TYPE: PRT
<213> ORGANISM: Artificial Sequence
<220> FEATURE:
<223> OTHER INFORMATION: Artificially synthesized peptide sequence

<400> SEQUENCE: 1

Leu Gly Ile Ser Tyr Gly Arg Lys Lys Arg Arg Gln Arg Arg Arg Pro
 1               5                  10                  15

Pro Gln

<210> SEQ ID NO 2
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 2
gggcgtgaat tctagttatt aatagtaa                                             28

<210> SEQ ID NO 3
<211> LENGTH: 33
<212> TYPE: DNA
<213> ORGANISM: Artificial Sequence
```

```
<220> FEATURE:
<223> OTHER INFORMATION: Artificially synthesized primer sequence

<400> SEQUENCE: 3
gggcggaatt ccgcttacaa tttacgcctt aag                          33

<210> SEQ ID NO 4
<211> LENGTH: 16
<212> TYPE: PRT
<213> ORGANISM: Artificial Sequence
<220> FEATURE:
<223> OTHER INFORMATION: Artificially synthesized peptide sequence

<400> SEQUENCE: 4

Arg Gln Ile Lys Ile Trp Phe Gln Asn Arg Arg Met Lys Trp Lys Lys
 1               5                  10                  15

<210> SEQ ID NO 5
<211> LENGTH: 30
<212> TYPE: PRT
<213> ORGANISM: Artificial Sequence
<220> FEATURE:
<223> OTHER INFORMATION: Artificially synthesized peptide sequence

<400> SEQUENCE: 5

Val Ala Tyr Ile Ser Arg Gly Gly Val Ser Thr Tyr Tyr Ser Asp Thr
 1               5                  10                  15

Val Lys Gly Arg Phe Thr Arg Gln Lys Tyr Asn Lys Arg Ala
            20                  25                  30

<210> SEQ ID NO 6
<211> LENGTH: 20
<212> TYPE: PRT
<213> ORGANISM: Artificial Sequence
<220> FEATURE:
<223> OTHER INFORMATION: Artificially synthesized peptide sequence

<400> SEQUENCE: 6

Met Leu Gly Ile Ser Tyr Gly Arg Lys Lys Arg Arg Gln Arg Arg Arg
 1               5                  10                  15

Pro Pro Gln Thr
            20

<210> SEQ ID NO 7
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 7
aattcggcgg ccgcgagct                                          19

<210> SEQ ID NO 8
<211> LENGTH: 11
<212> TYPE: DNA
<213> ORGANISM: Artificial Sequence
<220> FEATURE:
<223> OTHER INFORMATION: Artificially synthesized primer sequence

<400> SEQUENCE: 8
cgcggccgcc g                                                  11
```